United States Patent [19]
McFall et al.

[11] Patent Number: 5,993,431
[45] Date of Patent: *Nov. 30, 1999

[54] EXTENSIBLE CRIMP SEAL FOR FEMININE HYGIENE PRODUCTS

[75] Inventors: Ronald Ray McFall; David Christopher Oetjen, both of West Chester, Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/886,057

[22] Filed: Jun. 30, 1997

[51] Int. Cl.⁶ ...................................................... A61F 13/15
[52] U.S. Cl. .................... 604/385.2; 604/358; 604/385.1
[58] Field of Search ................................. 604/358, 385.1, 604/385.2

[56] References Cited

U.S. PATENT DOCUMENTS

| | | |
|---|---|---|
| 3,599,640 | 8/1971 | Larson . |
| 3,828,784 | 8/1974 | Zoephel . |
| 4,205,679 | 6/1980 | Repke et al. . |
| 4,662,874 | 5/1987 | Korpman . |
| 4,911,701 | 3/1990 | Mavinkurve . |
| 5,013,382 | 5/1991 | Nalowaniec et al. . |
| 5,429,630 | 7/1995 | Beal et al. ............................ 604/385.1 |
| 5,518,801 | 5/1996 | Chappell et al. . |
| 5,611,790 | 3/1997 | Osborn, III et al. . |

FOREIGN PATENT DOCUMENTS

| | | |
|---|---|---|
| WO 93/01786 | 4/1993 | WIPO . |
| WO 95/20931 | 8/1995 | WIPO . |
| WO 96/23472 | 8/1996 | WIPO . |

*Primary Examiner*—John G. Weiss
*Assistant Examiner*—Dennis Ruhl
*Attorney, Agent, or Firm*—Jeffrey V. Bamber

[57] ABSTRACT

A liquid impervious seal for extensible absorbent articles for wearing in an undergarment, such as sanitary napkins, panty liners, incontinence pads, and the like, is disclosed. The absorbent articles are typically formed from the following components: a liquid pervious topsheet, a liquid impervious backsheet joined to the topsheet, and an absorbent core positioned between the topsheet and backsheet. The components forming the absorbent article are held together by use of an extensible liquid impervious seal having a sinusoidal configuration.

4 Claims, 3 Drawing Sheets

EXTENSIBLE CRIMP SEAL FOR FEMININE HYGIENE PRODUCTS

FIELD OF THE INVENTION

The present invention relates to absorbent articles such as sanitary napkins, panty liners, incontinence devices, and the like. More particularly, the present invention relates to absorbent articles of the foregoing type that are extensible and preferably elastically extensible in multiple directions.

BACKGROUND OF THE INVENTION

Absorbent articles such as sanitary napkins, pantiliners, and incontinence pads are designed to absorb and retain liquid and other discharges from the human body and to prevent body and clothing soiling. Sanitary napkins are a type of absorbent article worn by women that is normally positioned between the wearer's legs, adjacent to the perineal area of the body.

Typically, most of the disposable absorbent articles of the types mentioned above are made of materials that will not stretch. That is, the materials (and the article itself) will not stretch under the forces that the absorbent article is normally subjected to when worn.

The inability of the absorbent articles to stretch causes such articles to have a number of serious drawbacks. One of the most serious is that they are not as comfortable for the wearer as they could be. The wearer should ideally be able to notice a difference between an absorbent article that stretches to conform to the wearer's body and with the wearer's movements and an absorbent article that fails to stretch. Conventional sanitary napkins will also fail to stretch and move with the wearer's undergarments, which may cause the sanitary napkins to shift therein. Providing the sanitary napkin with stretch properties will permit the napkin to better conform to the wearer's undergarment and stay in place.

Several patent publications disclose absorbent articles having various components that are capable of stretching. Such efforts are described in U.S. Pat. No. 2,701,567 issued to Smith, U.S. Pat. No. 3,570,493 issued to Olsson, U.S. Pat. No. 3,653,382 issued to Easley, et al., U.S. Pat. No. 3,717,150, issued to Schwartz, U.S. Pat. No. 4,013,816 issued to Sabee, et al., U.S. Pat. No. 4,041,949 issued to Kozak, U.S. Pat. No. 4,166,464 issued to Korpman, U.S. Pat. No. 4,533,357 issued to Hall, U.S. Pat. No. 4,573,991 issued to Pieniak, et al., U.S. Pat. No. 4,578,070 issued to Holtman, U.S. Pat. No. 4,596,570 issued to Jackson, et al., U.S. Pat. No. 4,655,760 issued to Morman, et al. U.S. Pat. No. 4,731,066 issued to Korpman, U.S. Pat. No. 4,847,134 issued to Fahrenkrug, et al., U.S. Pat. No. 4,891,258 issued to Fahrenkrug, et al., U.S. Pat. No. 4,965,122 issued to Morman, U.S. Pat. No. 4,992,324 issued to Dube, U.S. Pat. No. 5,011,480 issued to Gossens, et al., and European Patent Application 0 450 541 A2 published in the name of Morris, et al.

Some of the publications listed above disclose providing absorbent articles with one or more stretchable components. More recently, various embodiments of absorbent articles, such as sanitary napkins, comprised entirely of components capable of stretching to accommodate the movements of the wearer and the wearer's undergarments have been disclosed in U.S. Pat. No. 5,611,790 entitled "Stretchable Absorbent Articles", issued to Osborn, et al. on Mar. 18, 1997. Improved materials for use in absorbent articles have also been developed.

For example, U.S. Pat. No. 5,518,801 entitled "Web Materials Exhibiting Elastic-Like Behavior", issued to Chappell, et al. on May 21, 1996, discloses web materials which exhibit an elastic-like behavior and absorbent articles embodying such materials. U.S. Pat. No. 5,560,878 entitled "Method and Apparatus for Making Stretchable Absorbent Articles", issued to Dragoo, et al. on Oct. 1, 1996, discloses a stretchable absorbent material. PCT Publication No. WO 95/20931, entitled "Absorbent Articles" published in the name of Osborn, et al. on Aug. 10, 1995 is directed to extensible absorbent articles that are provided with improved mechanisms for maintaining the articles in contact with the wearer's body. The search for improved variations of extensible absorbent articles, and absorbent cores for such absorbent articles, however, has continued.

It is, therefore, an object of this invention to provide an improved absorbent article, such as a sanitary napkin, that is capable of extending, or more preferably, one that is elastically extensible.

It is another object of this invention to provide an absorbent article, such as a sanitary napkin, that is capable of elastic extensibility in multiple directions.

It is another object of the present invention to provide extensible absorbent articles that are provided with improved mechanisms for preventing some of the problems that affect such generally highly flexible absorbent articles, such as the undesirable tendency for the end regions of the absorbent articles to fold over on the remainder of the absorbent article.

It is another object of the present invention to provide an extensible absorbent article with diagonal extensibility to accommodate the forces walking, and similar motions exert on the absorbent article when it is attached to the wearer's undergarments.

It is another object of the present invention to provide improved absorbent cores for extensible absorbent articles.

It is another object of the present invention to provide an absorbent article with side flaps or wings that have portions that are extensible for relieving stresses on the sanitary napkin when the flaps are wrapped around the side edges of a wearer's undergarments.

It is still another object of the present invention to provide an extensible absorbent article with an improved type of stretchable crimp seal that joins the extensible components of the absorbent article together yet still allows them to extend.

These and other objects of the present invention will be more readily apparent when considered in reference to the following description and when taken in conjunction with the accompanying drawings.

SUMMARY OF THE INVENTION

The present invention provides a multi-directionally extensible, and preferably elastically extensible, absorbent article for wearing in an undergarment, such as a sanitary napkin, panty liner, incontinence device, or the like.

The multi-directionally extensible absorbent article has a longitudinal centerline, a transverse centerline, a pair of longitudinal side edges, a pair of end edges, a first end region, a second end region, and a central region between the first and second end regions. The multi-directionally extensible absorbent article preferably has a main body portion that comprises at least two regions that are extensible in different directions, and at least one of these regions, and preferably two or more of these regions, are capable of 25% elongation under forces of less than or equal to about 500 grams. The main body portion of the multi-directionally extensible absorbent article preferably comprises a multi-directionally extensible liquid pervious topsheet, a multi-directionally extensible liquid impervious backsheet at least partially peripherally joined to the topsheet, and a multi-directionally extensible absorbent core positioned between the topsheet and the backsheet.

In one preferred embodiment, the main body portion of the multi-directionally extensible absorbent article has a central region that is primarily extensible in the transverse direction. The first and second end regions preferably each comprise three regions of extensibility: a first region of extensibility, a second region of extensibility, and a third region of extensibility. The first region of extensibility in the end regions is disposed along at least a portion of the longitudinal centerline adjacent one of the end edges of the main body portion. The first region of extensibility is primarily extensible in the transverse direction. The second region of extensibility is disposed laterally outward of at least part of the first region of extensibility on one side of said first region of extensibility, and extends toward one of the longitudinal side edges of the absorbent article. The second region of extensibility is extensible in a direction which is between the longitudinal and transverse directions. The third region of extensibility is disposed laterally outward of at least part of the first region of extensibility on the other side of the first region of extensibility. The third region of extensibility extends toward the other longitudinal side edge of the absorbent article, and is extensible in a direction which is between the longitudinal and transverse directions.

In this or other embodiments, the multi-directionally extensible absorbent article can be provided with side flaps or wings that extend laterally outward beyond the longitudinal side edges of the main body portion of the absorbent article. The side flaps have an improved configuration of portions therein that are extensible for relieving stresses on the flaps when they are wrapped around the side edges of a wearer's undergarments. More specifically, the side flaps are integral with the main body portion, and are provided with extensibility in zones that are located inward of the edge of the absorbent core of the absorbent article. It is also within the scope of the present invention for the flaps described herein to be utilized on conventional non-extensible absorbent articles.

In addition, the components forming the extensible absorbent article are preferably held together by use of a novel liquid impervious seal having a sinusoidal configuration that allows the components to extend elastically.

DETAILED DESCRIPTION OF THE INVENTION

Figure 1:
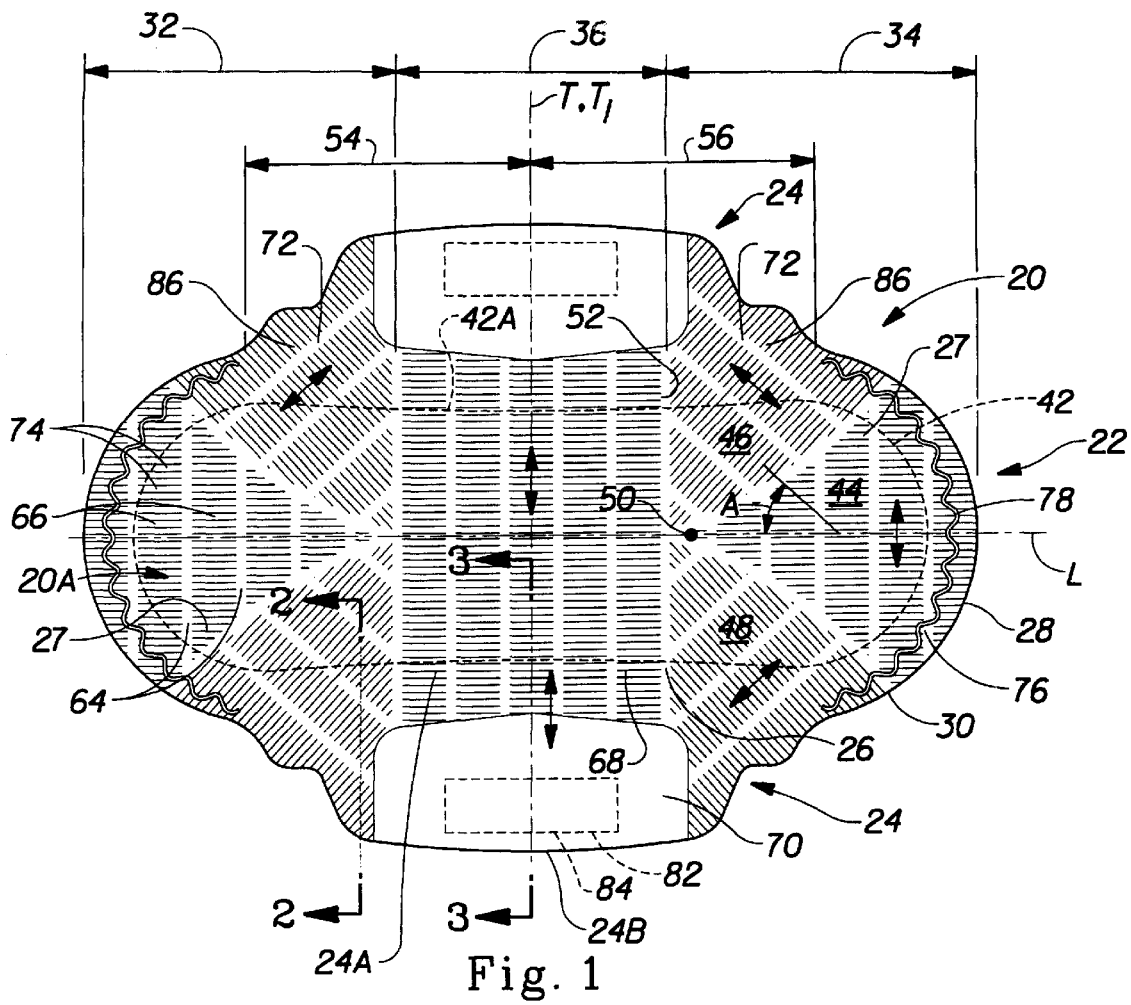
FIG. 1 is a top plan view of a preferred sanitary napkin embodiment of the present invention.

FIGS. 1–4 show a preferred embodiment of a disposable absorbent article comprising the present invention. The present invention relates to absorbent articles that are worn in an undergarment, such as sanitary napkins, panty liners, incontinence devices, and the like.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, and incontinence pads (and other articles worn in the crotch region of a garment).

The term "disposable" refers to articles which are intended to be discarded after a single use and preferably recycled, composted, or otherwise disposed of in an environmentally compatible manner. (That is, they are not intended to be laundered or otherwise restored or reused as an absorbent article.) In the preferred embodiment illustrated, the absorbent article is a sanitary napkin designated 20.

The term "sanitary napkin", as used herein, refers to an article which is worn by females adjacent to the pudendal region that is intended to absorb and contain the various exudates which are discharged from the body (e.g., blood, menses, and urine). The present invention, however, is not limited to the particular types or configurations of absorbent articles shown in the drawings.

The sanitary napkin 20 has two surfaces, a body-contacting surface or "body surface" 20A and a garment surface 20B. The sanitary napkin 20 is shown in FIG. 1 as viewed from its body surface 20A. The body surface 20A is intended to be worn adjacent to the wearer's body. The garment surface 20B is intended to be placed adjacent to the wearer's undergarments when the sanitary napkin 20 is worn.

The sanitary napkin 20 has two centerlines, a principal longitudinal centerline (or "longitudinal centerline") L and a principal transverse centerline (or "transverse centerline") T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

As shown in FIG. 1, the sanitary napkin 20 preferably comprises a main body portion 22 and two flaps 24. FIG. 1 shows that the main body portion 22 of the sanitary napkin 20 comprises the portion of the sanitary napkin without the flaps 24. The main body portion 22 has two spaced apart longitudinal edges 26, two spaced apart transverse or end edges (or "ends") 28, which together form the periphery 30 of the main body portion. The main body portion 22 has four corners 27 where the longitudinal edges 26 and end edges 28 converge. The main body portion 22 also has two end regions, which are designated first end region 32 and second end region 34. A central region 36 is disposed between the end regions 32 and 34. The end regions 32 and 34 extend outwardly in the longitudinal direction from the edges of the central region 36 about ⅛ to about ⅓, or more, of the length of the main body portion. A detailed description of the characteristics of a central region and two end regions for a sanitary napkin is contained in U.S. Pat. No. 4,690,680 issued to Higgins on Sep. 1, 1987.

The main body portion 22 of the sanitary napkin 20 can be of any thickness, including relatively thick, intermediate thickness, relatively thin, or even very thin (or "ultra thin"). The characteristics of generally inextensible "ultra thin" sanitary napkins are described in U.S. Pat. Nos. 4,950,264 and 5,009,653 issued to Osborn. The embodiment of the sanitary napkin 20 shown in FIGS. 1–3 of the drawings is intended to be an example of an ultra-thin sanitary napkin which has a caliper of about 4 millimeters. The main body portion 22 of the sanitary napkin 20 is also preferably relatively flexible, so that it is comfortable for the wearer.

The sanitary napkin 20 shown in the drawings is extensible, preferably stretchable, and more preferably elastically stretchable, in multiple directions. The term "extensible", as used herein, refers to articles that can increase in at least one of their dimensions in the x-y plane. The x-y plane is a plane generally parallel to the faces of the sanitary napkin 20. The term "extensible" includes articles that are stretchable and elastically stretchable. The term "stretchable", as used herein, refers to articles that are extensible when stretching forces are applied to the article and offer some resistance to stretching.

Figure 5:
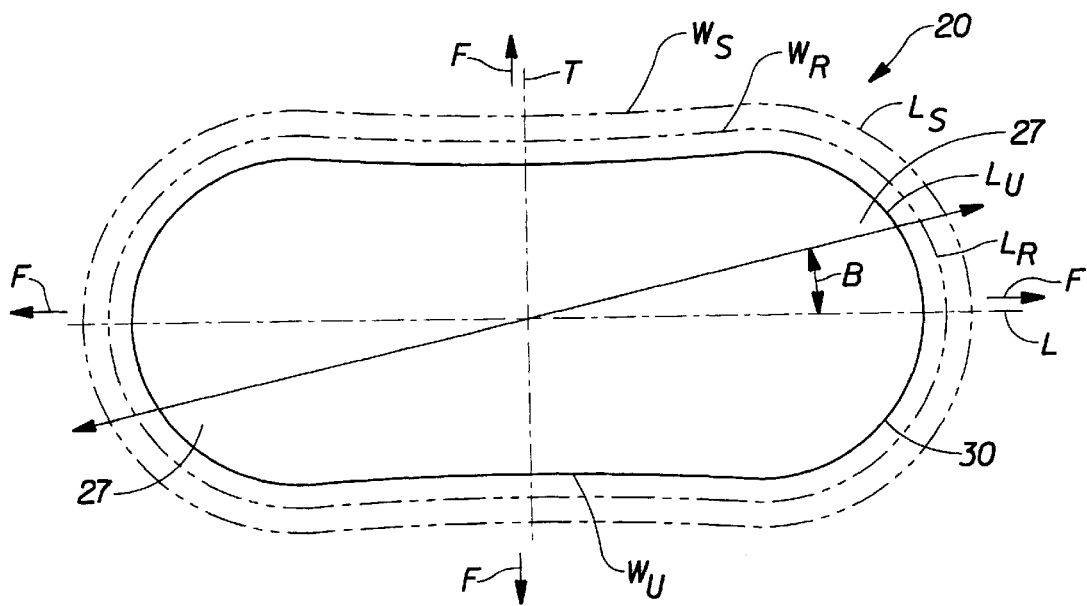
FIG. 5 is a simplified plan view of a sanitary napkin after stretching.

The terms "elastically stretchable" or "elastically extensible" are intended to be synonymous. These terms are illustrated with the simplified schematic view of the sanitary napkin in FIG. 5. As shown in FIG. 5, the sanitary napkin 20 can extend to a stretched length $L_S$ and a stretched width $W_S$. As used herein, the terms "elastically stretchable" or "elastically extensible" mean that when the stretching forces designated "F" are removed, the sanitary napkin will tend to return toward its unextended or unstretched dimensions (or "original" dimensions $L_u$ and $W_u$. The sanitary napkin 20 need not return all the way to its unstretched dimensions, however. It may, as shown in FIG. 5, return to relaxed dimensions (such as $L_R$ and $W_R$) between its unstretched dimensions ($L_U$ and $W_U$) and its extended (or stretched dimensions) $L_S$ and $W_S$.

Figure 2:
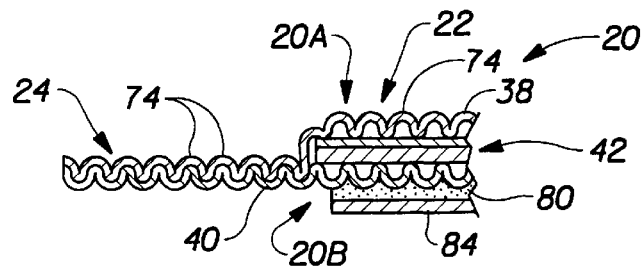
FIG. 2 is a lateral cross-sectional view taken along line 2—2 of FIG. 1 through the corner region of one of the flaps of the sanitary napkin.
Figure 3:
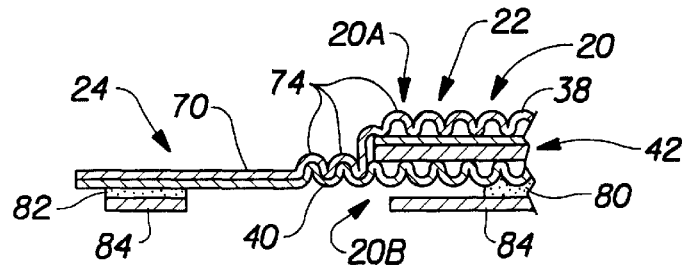
FIG. 3 is a lateral cross-sectional view taken along line 3—3 of FIG. 1 through the center portion of one of the flaps.

FIG. 2 shows the individual components of the main body portion 22 of the sanitary napkin 20 of the present invention. The main body portion 22 of the sanitary napkin preferably comprises at least three primary components. These include a liquid pervious topsheet 38, a liquid impervious backsheet 40, and an absorbent core 42 positioned between the topsheet 38 and the backsheet 40. The liquid pervious topsheet, the liquid impervious backsheet, and the absorbent core can comprise a number of suitable materials, provided that they are extensible as described below, or comprise base materials that are suitable for being modified as specified herein to provide them with extensibility.

In the embodiment shown in FIG. 1, the base material for the liquid pervious topsheet 38 comprises an apertured formed film. Suitable formed films are described in U.S. Pat. No. 3,929,135, issued to Thompson on Dec. 30, 1975; U.S. Pat. No. 4,324,245, issued to Mullane, et al. on Apr. 13, 1982; U.S. Pat. No. 4,342,314, issued to Radel, et al. on Aug. 3, 1982; U.S. Pat. No. 4,463,045, issued to Ahr, et al. on Jul. 31, 1984; and U.S. Pat. No. 5,006,394, issued to Baird, on Apr. 9, 1991. One especially preferred base material for the topsheet 38 comprises a formed film described in one or more of the above patents and marketed on sanitary napkins by The Procter & Gamble Company of Cincinnati, Ohio as the "DRI-WEAVE" topsheet. The base material for the topsheet 38 preferably has a hydrophilic surfactant incorporated therein during manufacture. The base material for the topsheet 38 is modified to make it multi-directionally extensible as discussed in greater detail below.

The absorbent core 42 can comprise a variety of absorbent materials which are capable of extensibility, or are suitable for being modified to make them extensible. For example, materials suitable for use as the absorbent core 42 could comprise a knit material, or a nonwoven material that is modified to make it multi-directionally extensible. The phrase "multi-directionally" extensible, as used herein, refers to extensibility in at least two directions in the x-y plane. (It should also be understood that the materials described herein for use in the absorbent core 42 can optionally be used as absorbent cores in other types of disposable absorbent articles, such as disposable diapers, and the like, if desired.)

One suitable multi-directionally elastically extensible nonwoven material is a 50/50 blend of polymeric fibers, such as polyester fibers and a fibrous superabsorbent hydrogel-forming polymeric material (or "absorbent gelling material"). A suitable fibrous absorbent gelling material is obtained as product #1161 from Camelot Superabsorbents, Ltd. of Calgary, Alberta, Canada. The nonwoven material is preferably embossed with the pattern described in U.S. Pat. No. 4,781,710 issued to Megison, et al. The embossed nonwoven material is preferably then heated to a temperature of just below the glass transition temperature of the polyester (about 280° F. (about 138° C.)) and consolidated laterally as described in University of Tennessee U.S. Pat. No. 5,244,482 entitled "Post-Treatment of Nonwoven Webs" issued to Hassenboehler, Jr., et al. on Sep. 14, 1993, so that it will be extensible in a first direction.

The nonwoven web is then preferably cooled to about 200° F. (about 93° C.) and mechanically compressed (or "micrexed") to provide it with extensibility in a second direction perpendicular to the first direction. Suitable methods for mechanically compressing nonwoven webs are described in U.S. Pat. No. 3,260,778 issued to Walton on Jul. 12, 1966; U.S. Pat. No. 3,426,405 issued to Walton on Feb. 11, 1969; and U.S. Pat. No. 5,117,540 issued to Walton, et al. on Jun. 2, 1992. The entire process can produce a nonwoven absorbent core material that is extensible about 25% in both the machine direction (the direction the fabric unwinds from a roll in the process of manufacturing the sanitary napkin 20) and the cross-machine direction (perpendicular to the direction of unwinding) under forces of less than or equal to about 200 grams/inch (about 80 g/cm), preferably less than or equal to about 100 grams/inch (about 40 g/cm), more preferably between about 25 to about 100 grams/inch (about 10 to about 40 grams/cm), and most preferably about 60 grams/inch (about 24 grams/cm).

The absorbent core 42 in the embodiment shown in the drawings preferably comprises a omni-directionally elastically extensible knit material. The phrase "omni-directionally" extensible, as used herein, refers to extensibility in all directions in the x-y plane. In a particularly preferred embodiment, the absorbent core 42 is a laminate of two or more knit materials. Preferably, the absorbent core 42 comprises a three layer structure comprising layers of knit Nylon material, knit polyester material, and knit 20/1

Acrylic material that are sewn together with stitching that provides the laminate with a jacquard quilted pattern. Such a material is known as product number B7112 and obtained from Flynt Amtex, Inc. of Burlington, N.C. The Flynt material has a basis weight of 24 mg/cm$^2$, an absorbent capacity of greater than or equal to about 5 grams of water per gram of fabric, and a caliper of about 2 mm. A simple test for determining the capacity of such a material is described below in the Test Methods section.

The absorbent core 42 (e.g., the Flynt material) is preferably capable of omni-directional extension in the following amounts at the forces specified: 5% elongation under a force of less than or equal to about 20 grams/inch (about 8 g/cm); 10% elongation under a force of less than or equal to about 35 grams/inch (about 14 g/cm); 25% elongation under a force of less than or equal to about 200 grams/inch (about 80 g/cm), preferably less than or equal to about 100 grams/inch (about 40 g/cm), more preferably less than or equal to about 85 grams/inch (about 33 g/cm); and 50% elongation under a force of less than or equal to about 225 grams/inch (about 90 g/cm). All forces specified herein are measured with one inch (2.54 cm) wide strip of the absorbent material as described in the Test Methods section below. For simplicity, omni-directional extensibility is measured using strips cut in the longitudinal direction, the transverse direction, and a 45 degree diagonal direction.

The absorbent core 42 (e.g., the Flynt material) is preferably omni-directionally elastically extensible. The absorbent core 42 may, but need not return all the way to its unextended dimensions when the extending forces are removed. This feature can be expressed in terms of percent (%) set of the core material. The Flynt material has less than or equal to about 10% set in the longitudinal direction, transverse direction, and the diagonal direction.

The absorbent core 42 (e.g., the Flynt material) is preferably highly flexible and drapable. The Flynt material has a Taber Stiffness of about 0.11 or 0.12 g cm; a flexural rigidity of about 26 mg cm/cm; and a flexure resistance of about 14 or 15 grams measured on the Flynt material alone using the test set out in U.S. Pat. No. 5,009,653 issued to Osborn. The Flynt material has one side with a "puffy" appearance, and one side which is relatively flat. The Flynt material can be placed in the sanitary napkin 20 with either side adjacent to the topsheet 38. No modification of this absorbent core material is necessary since it is inherently omni-directionally extensible.

In certain cases, it may be desirable to provide the Flynt material with additional absorbent capacity for use as the absorbent core 42. This can be done in several non-limiting ways. In one embodiment, an additional web or strip of extensible material can be joined to the underside of the Flynt material. In this embodiment, the additional web or strip of extensible material can have its surface which will be placed adjacent to the Flynt material (that is, its inside surface) provided with absorbent gelling material thereon. The additional web or strip, therefore, "traps" or holds the absorbent gelling material adjacent to the underside of the Flynt material.

In one preferred version of such an embodiment, the extensible material comprises a rectangular strip about 2 inches (about 5 cm) wide and about 6.25 inches (about 16 cm) long of an air-through bonded nonwoven material comprised of bi-component fibers which is manufactured under the tradename HAVIX S2146 by the Havix Corporation, Gifu-City, Japan. The HAVIX material will have a degree of extensibility in one direction, which is preferably its widthwise direction. The HAVIX material is preferably mechanically compressed (or "micrexed") as described in conjunction with the multi-directionally extensible nonwoven material discussed above so that it is also extensible in the longitudinal direction. The absorbent gelling material is preferably applied to the HAVIX material as a mixture of Nalco 1180 absorbent gelling material obtained from Nalco Chemical Company, Naperville, Ill., and PEGOSPERSE surfactant obtained from Lonza, Inc., Williamsport, Pa. These components are preferably mixed together in a ratio of about 10 grams of absorbent gelling material to about 1 gram of surfactant. Preferably, about 0.3 to about 0.4 grams of this mixture is applied to the strip of HAVIX material.

The strip of HAVIX material can be joined to the underside of the Flynt material in any suitable manner. Preferably, the HAVIX material is stretched and joined to the underside of the Flynt material by use of an adhesive, such as adhesive number 2031 manufactured by Findley Adhesive Company of Wauwatosa, Wis. A double-sided adhesive tape can be placed around the perimeter of the HAVIX material for attachment to the Flynt material if additional securement is desired. The use of this additional web of material with the absorbent gelling material preferably nearly doubles the absorbent capacity of the sanitary napkin 20 from an overall capacity of about 12 grams to about 23 grams. These absorbent capacities are preferably measured according to the test set out in U.S. Pat. No. 5,009,653 issued to Osborn.

In other embodiments, the absorbent core 42 can be provided with additional capacity in other ways. For example, instead of adding a strip of material to the underside of the absorbent core as described above, the absorbent gelling material could be added on the surface of one or more of the layers of the absorbent core (such as one of the different layers of the Flynt material). Alternatively, one or more of the layers of the absorbent core could at least partially comprise fibrous absorbent gelling material.

The backsheet 40 can be any suitable liquid impervious material that is extensible, or comprises a base material that can be modified as specified herein to provide it with extensibility. Preferably, the base material for the backsheet 40 is a polyethylene film having a thickness of from about 0.012 mm (0.5 mil) to about 0.015 mm (2.0 mil). Exemplary polyethylene films are manufactured by Clopay Corporation of Cincinnati, Ohio, under the designation P18-0401 and microflex 1401. The backsheet 40 may be embossed and/or matte finished to provide a more clothlike appearance. Further, the backsheet 40 may permit vapors to escape from the absorbent core 42 (that is, it may be breathable) while still preventing exudates from passing through the backsheet. In a preferred embodiment when the base material for the backsheet 40 is produced, it is subjected to a corona discharge treatment in order to aid in gluing the desired portions of the same to the topsheet. Methods for treating a film material with a corona discharge are described in U.S. Pat. Nos. 4,351,784, 4,456,570, and 4,535,020 issued to Thomas, et al. The base material for the backsheet 40 is modified to make it multi-directionally extensible as discussed in greater detail below.

The topsheet 38, the backsheet 40, and the absorbent core 42 may be assembled in a variety of configurations known in the art (including layered or "sandwich" configurations and wrapped or "tube" configurations). FIGS. 1–4 show a preferred embodiment of the sanitary napkin 20 assembled in a sandwich construction in which the topsheet 38 and the backsheet 40 have length and width dimensions generally larger than those of the absorbent core 42. The topsheet 38 and the backsheet 40 extend beyond the edges of the absorbent core 42 to form portions of the periphery 30. The topsheet 38 is preferably joined to the body-facing side of the absorbent core 42. The topsheet 38 can be joined to the absorbent core 42 in any suitable manner known in the art for this purpose, such as by an open pattern of adhesives. The backsheet 40 need not be, and in the embodiment shown preferably is not, joined to the absorbent core 42. The portions of the topsheet 38 and backsheet 40 that extend beyond the edges of the absorbent core 42 to form the periphery 30, as will be described in greater detail below, are preferably joined to each other.

The topsheet 38 may be joined to the absorbent core 42 by a uniform continuous layer of adhesive, a patterned layer of adhesive, or an array of separate lines, spirals, or spots of adhesive. One adhesive that has been found to be satisfactory for this purpose is manufactured by Findley Adhesive Company of Wauwatosa, Wis. as adhesive number 2031. The adhesive is preferably applied an open pattern network of filaments of adhesive such as is disclosed in U.S. Pat. No. 4,573,986 entitled "Disposable Waste-Containment Garment", which issued to Minetola, et al. on Mar. 4, 1986. Other exemplary open pattern networks of adhesive filaments comprising several lines of adhesive filaments swirled into a spiral pattern are illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the components of the sanitary napkin may be joined by heat bonds, pressure bonds, ultrasonic bonds, dynamic mechanical bonds, or any other suitable attachment means or combinations of these attachment means as are known in the art.

The entire sanitary napkin 20, or regions of the same can be extensible in various directions. The multi-directionally extensible absorbent article preferably has a main body portion that comprises at least two regions that are extensible in different directions, and at least one of these regions, and preferably two or more of these regions, are capable of 25% elongation under forces of less than or equal to about 500 grams. In the embodiment shown in FIGS. 1–4, the central region 36 of the sanitary napkin 20 is generally extensible in the transverse direction. This is generally in the direction of the arrows shown in FIG. 1. As shown in the drawings, if the sanitary napkin 20 is provided with flaps 24, the extensibility of the central region 36 can extend into the flaps 24. The central region 36 expands laterally to assist the flaps 24 in folding around the curved side edges of the wearer's undergarments.

As used herein, the phrase "generally in the transverse direction" (or generally in another direction) means that a primary component of the extensibility is in the direction specified. All of the extension, however, need not be exactly in the direction specified. Therefore, when the extensibility is said to be generally in the transverse direction, the extensibility need not be exactly parallel to the principal transverse centerline of the sanitary napkin. The extensibility, however, is preferably oriented more in the transverse direction than in the longitudinal direction.

The first and second end regions 32 and 34 of the sanitary napkin 20 shown in FIGS. 1–4 each preferably comprise three regions of extensibility. The three regions of extensibility comprise a first region of extensibility 44, a second region of extensibility 46, and a third region of extensibility 48. In the embodiment shown in the drawings, the regions of extensibility in the first end region 32 of the sanitary napkin 20 are symmetrical with those same respective regions in the second end region 34, although in other embodiments, this need not be the case.

The first region of extensibility 44 of the end regions 32 and 34 is preferably disposed along at least a portion of the longitudinal centerline L of the sanitary napkin. A portion of the first region of extensibility 44 is preferably located adjacent to one of the end edges 28 of the main body portion 22. Preferably, the first region of extensibility 44 is a generally pie-shaped region that is centered relative to the longitudinal centerline. The first region of extensibility 44 preferably has a tip or apex 50 that lies along the longitudinal centerline, L. Preferably, the tip 50 extends substantially all the way to the end edge 52 of the central region 36. In the embodiment shown in the drawings, the first region of extensibility 44 is preferably also primarily extensible in the transverse direction (as shown by the arrows). This allows the first region to stretch with the wearer's panties, particularly in the region of the wearer's buttocks. The first and second end regions 32 and 34 preferably have the same extensibility so that the wearer can wear either end of the sanitary napkin 20 in the rear crotch portion of her panties.

The second region of extensibility 46 is disposed laterally outward of at least part of the first region of extensibility 44. The second region of extensibility 46 is located on one side of the first region of extensibility 44. The second region of extensibility 46 extends toward, and preferably to one of the longitudinal side edges 26 of the main body portion 22 of the sanitary napkin 20. As shown in the drawings, if the sanitary napkin 20 is provided with flaps 24, this region of extensibility can even extend beyond the longitudinal side edge 26 of the main body portion into the side flaps 24. In the embodiment shown in the drawings, the portion of the second region of extensibility 46 that overlies the main body portion 22 is preferably roughly in the shape of a right triangle.

In the embodiment shown in the drawings, the second region of extensibility 46 is extensible in a direction which is between the longitudinal and transverse directions. Preferably, in this embodiment, the second region of extensibility 46 is extensible in a direction having a primary vector component that forms an angle, A, as shown in FIG. 1, of between about 45° and about 55°, more preferably about 48° with the longitudinal centerline, L. The open portion of the angle A is turned so that the angle faces the transverse centerline, T, of the sanitary napkin 20. As long as the angle A is less than 90°, this provides "inwardly-oriented" extensibility, or extensibility having a primary vector component that is oriented inward toward the transverse centerline, T. This can be contrasted with regions having an "outward-oriented" extensibility, which have a primary vector component that is oriented away from the transverse centerline. Outward-oriented extensibility would be present if the extensibility was perpendicular to the arrows shown in region 46. The terms "inwardly-oriented" and "outwardly-oriented", refer to the direction of extensibility, rather than the direction in which the region may tend to retract which is also shown by one of the heads on each of the arrows in FIG. 1.

The third region of extensibility 48 is preferably disposed laterally outward of at least part of the first region of extensibility 44 on the other side of the first region of extensibility 44. The third region of extensibility 48 extends toward, and preferably to one of the longitudinal side edges 26 of the main body portion 22 of the sanitary napkin 20. The third region of extensibility 48 can also extend into the side flaps 24. The portion of the third region of extensibility 48 that overlies the main body portion 22 is also roughly in the shape of a right triangle. In the embodiment shown in the drawings, the third region of extensibility 48 is extensible in a direction which is between the longitudinal and transverse directions. Preferably, in this embodiment, the third region of extensibility 48 also has an inwardly oriented extensibility in a direction having a primary vector component that forms an angle of between about 45° and about 55°, more preferably about 48° with the longitudinal centerline, L. In the preferred embodiment shown in the drawings, the second and third regions of extensibility 46 and 48 are symmetrically disposed on either side of the first region of extensibility 44.

The sanitary napkin 20 differs from many prior absorbent articles in that it preferably has an overall extensibility that runs in diagonal directions. As used herein, "diagonal" means generally from one corner 27 of the main body portion to the corner 27 on the opposite side of the longitudinal and transverse centerlines. This is illustrated in FIG. 5. As shown in FIG. 5, the primary direction of overall extensibility of the main body portion 22 of the sanitary napkin 20 is preferably oriented in a direction that makes an angle B with the longitudinal centerline L. The angle B is greater than 0° and less than 45°, and is preferably between about 15° and about 30°, and for the embodiment shown in the drawings, is preferably about 20°.

It should be understood that the sanitary napkin 20 is preferably extensible in both diagonal directions that run between the four corners of the main body portion 22. Thus, not only does the sanitary napkin 20 have a primary component of extensibility that is oriented at the angle B shown in FIG. 5 (where the angle is turned counter clockwise relative to the longitudinal centerline L), but also at a similar angle turned clockwise relative to the longitudinal centerline L.

The amount of extensibility the sanitary napkin 20 is provided with is also important. The sanitary napkin 20 shown in the drawings is preferably capable of longitudinal extensibility along the longitudinal centerline, L, in the following amounts at the forces specified: 5% elongation under a force of less than or equal to about 200 grams; 10% elongation under a force of less than or equal to about 550 grams; 15% elongation under a force of less than or equal to about 900 grams; and 25% elongation under a force of less than or equal to about 1,600 grams. The sanitary napkin 20 is preferably elastically extensible in the longitudinal direction. The sanitary napkin 20 may have a small amount of set (up to about 10%) after it has been extended in the longitudinal direction.

The sanitary napkin 20 shown in the drawings is preferably capable of transverse extensibility in the central region 36 of the main body portion 22 measured along the transverse centerline, T, in the following amounts at the forces specified: 5% elongation under a force of less than or equal to about 75 grams; 10% elongation under a force of less than or equal to about 150 grams; 15% elongation under a force of less than or equal to about 250 grams; and 25% elongation under a force of less than or equal to about 400 grams. The sanitary napkin 20 shown in the drawings is preferably capable of transverse extensibility in the end regions 32 and 34 of the main body portion 22 measured parallel to the transverse centerline in approximately the same amounts and at the same forces. The sanitary napkin 20 is preferably elastically extensible in the transverse direction in the central region 36 and the end regions 32 and 34. The sanitary napkin 20 may have a small amount of set (up to about 10%) after it has been extended transversely in these regions.

The sanitary napkin 20 shown in the drawings is preferably capable of diagonal extensibility in the following amounts at the forces specified: 5% elongation under a force of less than or equal to about 200 grams; 10% elongation under a force of less than or equal to about 500 grams; 15% elongation under a force of less than or equal to about 850 grams; and 25% elongation under a force of less than or equal to about 1,500 grams. All forces specified herein are measured with one inch (2.54 cm) wide clamps as described in the Test Methods section below. The sanitary napkin 20 is preferably elastically extensible in the diagonal direction. The sanitary napkin 20 may have a small amount of set (up to about 10%) after it has been extended diagonally.

In the case of all of the directions of extensibility discussed in the preceding paragraphs, the sanitary napkin 20 is preferably not so highly extensible at low force levels that it is difficult to place the same in the wearer's undergarments. Preferably, the sanitary napkin 20 is not extensible in an amount greater than or equal to about 10% under forces of less than or equal to about 50 grams in each of the directions for which the extensibility is specified above. It should be understood, however, that this, like the extensibilities specified elsewhere herein are preferred amounts, and the absorbent articles of the present invention are not limited to those having extensibilities in the amounts described herein, unless otherwise specified in the appended claims.

The ability to stretch diagonally is made possible because of the direction of extensibility of the various regions of the topsheet 38 and backsheet 40, and the omni-directional extensibility of the preferred absorbent core 42 described herein. The overall diagonal extensibility provides the sanitary napkin 20 with several advantages. The diagonal extensibility helps the sanitary napkin to accommodate diagonal stretching of the wearer's panties associated with walking, and similar movements. The overall diagonal extensibility reduces tension on the sanitary napkin which may cause the undesirable tendency of the end edge portions of the sanitary napkin to fold over on the remainder of the main body portion 22 (that is, it prevents end edge "roll over", a problem which may lead to loss of coverage of, and soiling of the wearer's undergarments). Without wishing to be bound by any particular theory, it is believed that the reduction in end roll over is at least partially attributable to the fact that the sanitary napkin 20 is better able to accommodate the aforementioned diagonal stretching. In addition, designing a sanitary napkin with greater extensibility in a diagonal direction than in the longitudinal direction provides the sanitary napkin with more stiffness along the longitudinal centerline (than a sanitary napkin that has its greatest extensibility in the longitudinal direction), which will also tend to reduce end edge roll over.

The extensibility of the sanitary napkin 20 and the different regions thereof can be provided in any suitable manner. In the embodiment shown in the drawings, the extensibility is provided by forming a strainable network into the desired portions of the topsheet 38 and backsheet 40 of the sanitary napkin 20. The strainable network is formed by a process which may be referred to herein as forming the topsheet and backsheet base materials into a stretchable elastic-like film (or "SELFing" the topsheet and backsheet base materials). A suitable process for forming a strainable network into the topsheet 38 and backsheet 40 is described in U.S. Pat. No. 5,518,801 entitled "Web Materials Exhibiting Elastic-Like Behavior" which issued to Chappell, et al. on May 21, 1996.

As shown in FIG. 1, the topsheet 38 and backsheet 40 preferably have several strainable network regions formed therein. One strainable network region is formed for the central region 36 of the main body portion 22, and a strainable network region is formed for each of three regions of extensibility in the end regions 32 and 34 of the sanitary napkin 20. The different strainable network regions all preferably comprise portions of a single base topsheet or backsheet material that has a pattern of regions formed therein. In this embodiment, both the topsheet 38 and backsheet 40 have identical strainable network regions formed therein (though the strainable network is not shown on the backsheet 40 in FIG. 4 for simplicity of illustrating the adhesive pattern thereon). Preferably, the strainable networks in the topsheet 38 and backsheet 40 are aligned directly over one another.

As shown in FIGS. 1 and 2, each of the strainable networks comprise at least two visually distinct regions, first and second network regions 64 and 66. Preferably, each of the strainable networks comprises several first and second network regions 64 and 66. In the preferred embodiment shown, the first network regions 64 are substantially planar. The second network regions 66 preferably comprise a plurality of deformations in the form of raised rib-like elements 74.

The characteristics of the first and second network regions 64 and 66 can also be expressed in terms of the length of the respective regions measured topographically over the surfaces of these regions when the strainable network is in an untensioned condition (or the "surface-pathlength" of the first and second network regions). The second network region 66 has a surface-pathlength that is greater than that of the first network region 64. When elongation forces are applied to the strainable networks, the rib-like elements 74 will undergo a geometric deformation under which they will flatten and extend while the first regions will undergo a molecular level deformation. This will cause the strainable network regions to exhibit an elastic-like behavior in the direction of the arrows when subjected to an applied and subsequently released elongation. The general characteristics of strainable network regions are described in greater detail in U.S. Pat. No. 5,518,801 issued to Chappell, et al.

The strainable network(s) can be formed by separately feeding the base materials for the topsheet and backsheet between meshing patterned rolls, pressing the base material between mating plates having a pattern therein, or by casting. The strainable network(s) can be formed at several stages in the assembly of the components of the sanitary napkin 20 shown in the drawings. The strainable network(s) can be formed into the components of the sanitary napkin before they are joined together to form the sanitary napkin. Alternatively, the strainable network(s) can be formed into the entire assembled sanitary napkin. Preferably, in the embodiment shown in the drawings, the strainable network (s) are formed into the topsheet 38 and backsheet 40 before they are joined together to encase the absorbent core 42 therebetween. The absorbent core 42 may, but need not, have a strainable network formed therein since it preferably has multi-directional extensibility as described above. Preferably, in the embodiment illustrated in the drawings, the absorbent core 42 does not have a strainable network formed therein.

The portions of the topsheet 38 and backsheet 40 that extend beyond the edges of the absorbent core 42 form a flange 76. These portions of the topsheet 38 and backsheet 40 can be joined in any manner which does not interfere with the ability of the sanitary napkin to stretch. Preferably, in the embodiment shown, the topsheet 38 and backsheet 40 are joined using an extensible adhesive over substantially the entire portions that extend beyond the edges of the absorbent core 42, and a crimp seal 78 for added strength at the end edges 28 of the main body portion 22 where the topsheet 38 and backsheet 40 are densified by the application of pressure or heat and pressure. A suitable extensible adhesive is Fuller adhesive 2352 available from the H.B. Fuller Company of Badnais Heights, Minn. Preferably, a small amount of adhesive contacts the edges of the absorbent core 42 to keep the absorbent core 42 in position.

The crimp seal 78 should not interfere with the ability of the components of the sanitary napkin to stretch. Preferably, the extensible portions of the sanitary napkin that are joined by the crimp seal 78 are capable of extending the amounts and under the forces specified above for the sanitary napkin 20 (See e.g., the transverse extensibility in the end regions). (The crimp seal 78 is, however, capable of allowing the components to extend in multiple directions.) The crimp seal 78 may, thus, be referred to as an extensible crimp seal 78 (although the crimp seal 78 does not provide any inherent extensibility if not used with extensible components). The crimp seal 78 preferably comprises a liquid impervious seal. The crimp seal 78 preferably comprises a sinusoidal sealing line along which portions of at least one of the topsheet 38 or backsheet 40 are compressed and/or melted together. The crimp seal 78 shown in FIG. 1 is in a sinusoidal pattern that is preferably arranged in a generally curved configuration. Other configurations, such as straight sinusoidal patterns, can also be used. Without wishing to be bound by any particular theory, it is believed that the crimp seal 78 allows the portions of sanitary napkin adjacent thereto to extend because the waves of the sinusoidal configuration provide the crimp seal 78 with "slack" that can be stretched until it at least partially straightens.

Numerous variations of the extensible crimp seal 78 are possible. For example, the crimp seal can be located around all, or any portion of the periphery of the sanitary napkin including the distal edges of the flaps (described below). In addition to sinusoidal patterns, other suitable patterns which provide the desired "slack", including, but not limited to zig zag patterns can also be used. The extensible crimp seal 78 can have a sinusoidal (or other) pattern that varies in band width, amplitude, and frequency. In addition, multiple sinusoidal waves (or waves having other configurations) can be aligned in phase adjacent to each other. Such multiple crimp seals can be used to ensure that a continuous crimp is present around the desired portion of the perimeter of the sanitary napkin after processing. For example, it is possible to cut through a crimp seal during manufacture. This would most often occur when a web of sanitary napkins is cut at the end edges into individual sanitary napkins by the last cutting operation (or by the "final knife"). Multiple crimp seals will ensure that liquids will not wick through the crimp seal 78 even if a portion of the crimp seal is cut during manufacture.

In other embodiments, the continuous sinusoidal crimp seal can be combined with discontinuous (or intermittent) bonding patterns. The discontinuous bonding patterns can be in the form of discontinuous sinusoidal waves, or other suitable discontinuous patterns. The discontinuous patterns should be in configurations so that if any portion of the crimp seal is cut during manufacture, the discontinuous pattern will provide a tortuous flow path to trap any liquids that may attempt to wick through the crimp seal. These patterns may also provide increased manufacturing flexibility since the place where the final knife cut placement falls on the crimp is not as critical.

The extensible crimp seal 78 provides a number of advantages. These include, but are not limited to the following. The extensible crimp seal 78, of course, forms an impervious barrier to liquids wicking out of the ends 28 of the sanitary napkin 20. It also permits the components of the sanitary napkin to extend, even though it is continuous. It was previously believed that a discontinuous bonding pattern had to be used to avoid interfering with the ability of the components of an extensible absorbent article to extend. The extensible crimp seal 78 also helps to prevent the undesirable tendency for the end edge portions of the sanitary napkin to fold over on the remainder of the main body portion. Without wishing to be bound to any particular theory, it is believed that this occurs because the extensible crimp seal 78 eliminates any differences in extensibility between the flange 76 and the remainder of the main body portion 22 that would cause the flange 76 to curl when the main body portion 22 is stretched.

The sanitary napkin 20 shown in FIGS. 1–4, also comprises a pair of flaps 24 that are joined to the main body portion 22. The flaps 24 extend laterally outward beyond the longitudinal side edges 26 of the main body portion 22 from their proximal edges 24A to their distal edges (or "free ends") 24B. The flaps 24 extend outward from at least the central region 36 of the main body portion 22. As shown in FIG. 1, each flap 24 is divided into a front half 54, and a back half 56 by a flap transverse centerline $T_1$. The flap transverse centerline $T_1$ may coincide with the principal transverse centerline T of the sanitary napkin, but this is not absolutely required. The flaps 24 are each joined to (or associated with) main body portion 22 along a juncture. This is typically a longitudinally-oriented (or "longitudinal") juncture, such as lines of juncture 68. As used herein, the terms "juncture" (or "line of juncture") refer to regions where the flaps 24 extend from or are joined to the main body portion 22.

The flaps 24 can be joined to the main body portion 22 in any suitable manner. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. Preferably, in the embodiment shown in FIGS. 1–4, the flaps 24 are integral with the main body portion 22 (that is, the flaps 24 comprise integral extensions of the topsheet 38 and backsheet 40).

The extensions of the topsheet 38 and backsheet 40 comprising the flaps 24 may be joined together in any suitable manner. For example, the extensions of the topsheet 38 and backsheet 40 that form the flaps can be joined together by adhesives over their entire interface, or any suitable portion thereof, to form the flaps 24. Preferably, the extensions of the topsheet 38 and backsheet 40 comprising the flaps 24 (like those portions that form the flange 76) are joined together over their entire interface with a continuous layer of extensible adhesive such as Fuller adhesive 2352.

The flaps 24 can be in any suitable configuration. Suitable flaps are described in Reexamined Patent No. B 1 4,589,876 entitled "Sanitary Napkin", issued to Van Tilburg, Certificate of Reexamination issued Apr. 27, 1993; U.S. Pat. No. 4,687,478 entitled "Shaped Sanitary Napkin With Flaps", which issued to Van Tilburg on Aug. 18, 1987; U.S. Pat. No. 5,389,094 entitled "Absorbent Article Having Flaps and Zones of Differential Extensibility" issued to Lavash, et al. on Feb. 14, 1995; and in International Patent Application Serial No. PCT US 96/15957 entitled "Absorbent Article Having Flaps With Step Configuration and Zones of Extensibility" filed on Oct. 3, 1996, in the name of Lash, et al.

In a preferred embodiment, the sanitary napkin 20 has several improved characteristics for relieving stresses on the main body portion 22 and on the flaps 24 when the flaps 24 are wrapped around the side edges of a wearer's undergarment.

One improved characteristic described above is that central region 36 of the main body portion 22 is provided with lateral extensibility. This allows the central region 36 to expand to assist the flaps 24 in folding around the curved side edges of the wearer's undergarments. As shown in FIG. 1, the transverse extensibility also preferably extends from the central region 36 of the main body portion 22 laterally outward beyond the longitudinal side edges 26 of the main body portion 22 into the flaps 24. In the embodiment shown, this laterally extensible region preferably terminates at a region 70 surrounding the flap adhesive 82. The region surrounding the flap adhesive 70 is preferably stiffer than the remainder of the flap 24 to aid in handling the flaps 24 when the consumer uses the same.

Another improved characteristic is that in the embodiment shown, even though the side flaps 24 are integral with the main body portion 22, they are provided with zones of extensibility 72 that originate at a point located inward of the longitudinal side edge 42A of the absorbent core 42 of the sanitary napkin 20 (that is, in the second and third regions of extensibility 46 and 48). It is desirable to have zones of extensibility 72 located inward of the longitudinal side edges 42A of the absorbent core 42 for several reasons. First, by starting the extensibility inward of the longitudinal edges 42A of the absorbent core 42, the overall amount of extensibility that the flaps 24 can be provided with can be significantly increased relative to flaps having all of their extensibility located laterally outward of the absorbent core 42. Second, the extensibility can more effectively fit a wider variety of panty sizes and styles when it is located inwardly of the longitudinal edges 42A of the absorbent core 42. The difficulty with providing the sanitary napkin having integral flaps with extensibility that is located inwardly of the edges of the absorbent core was that the absorbent core was typically both inextensible and too thick to form strainable network regions therein. In the embodiment shown in the drawings, however, these difficulties are overcome by utilizing an extensible absorbent core 42 which is surrounded by a topsheet 38 and backsheet 40 which both have the desired extensible regions formed therein, and joining the topsheet 38 and backsheet 40 together.

The extensible portions of the topsheet and backsheet are vertically aligned with the strainable network regions in the topsheet 38 lying directly over those in the backsheet 40. The extensible portions of the topsheet 38 and backsheet 40 can be joined to the absorbent core 42 and extend with the absorbent core. Alternatively, either one, or both of the topsheet 38 and backsheet 40 can be unattached to the absorbent core 42 in these regions. Preferably, at least the backsheet 40 is unattached to the absorbent core 42 in these regions.

Still another improved characteristic of the sanitary napkin 20 in the embodiment shown in the drawings is the direction of the primary vector component of extensibility in the corner regions 86 of the flaps 24 and the adjacent portions of the main body portion 22 (the second and third regions of extensibility 46 and 48). The corner regions 86 of the flaps occur where the outer edges of the flaps 24 intersect with the longitudinal side edges 26 of the main body portion 22 when the sanitary napkin 20 is shown in plan view. The corner regions 86 include not only these corners, but also surrounding regions and adjacent regions inboard of the edges of the flaps 24. It is also not necessary for there to be a sharp angle formed at the intersection of these edges, or for lines of demarcation to designate the same. A more detailed description of the corner regions for a sanitary napkin having flaps is contained in U.S. Pat. No. 5,389,094 issued to Lavash, et al. The corner regions 86 of the embodiment shown in FIG. 1 are located in the same region as the zones of extensibility 72.

The direction of the primary vector component of extensibility in the corner regions 86 in various embodiments can be primarily in the transverse direction, primarily in the longitudinal direction, or in a direction between the transverse and longitudinal directions. In the preferred embodiment shown in the drawings, the direction of the primary vector component of extensibility in the corner regions 86 is preferably in the same direction as that of the adjacent region of extensibility of the main body portion 22. The adjacent region of extensibility will be either the second or third regions of extensibility 46 and 48. Since these two regions of extensibility are preferably symmetrical, the relative direction of this primary vector component will generally be the same for both corner regions 86 of each flap 24. The term "relative direction" refers to the angle the primary vector component makes with the longitudinal centerline L. The relative direction of the primary vector component of extensibility of the corner regions 86 is, thus, at an angle A that faces inward toward the transverse centerline T of the sanitary napkin 20.

The inward orientation of the primary vector component of extensibility in the corner regions 86 provides several advantages. The extensibility is designed to more efficiently relieve the stresses on the flaps 24 when they are folded around the curved side edges of the wearer's undergarments than a number of previous attempts to solve this problem. In particular, the extensibility is intended to solve problems that are caused by the forces acting on both the main body portion 22 of the sanitary napkin 20 and the flaps 24 when the flaps 24 are wrapped around the curved side edges of the crotch region of the wearer's undergarments.

One such problem that the orientation of the extensibility described herein is intended to resolve is referred to herein as wing or flap "pop off". This involves the flap adhesive 82 (described in greater detail below), which is designed to secure the flaps 24 around the undergarment by attaching the flaps 24 to the underside of the wearer's undergarment, or to the opposing flap. Folding the flaps 24 around the side edges of the wearer's undergarments causes tension to be placed on the flaps. This tension may make the flap adhesive 82 lose its bond with the underside of the wearer's undergarment or with the opposing flap, and become unattached or "pop off" the same. One way to attempt to eliminate wing pop off is to increase the strength of the flap adhesive 82. However, increasing the strength of the flap adhesive 82 can lead to other problems.

Another problem that the orientation of the extensibility described herein is intended to resolve results from the fact that the tension created by folding the flaps 24 around the side edges of the wearer's undergarments can also place tension on the main body portion 22 of the sanitary napkin 20. This is particularly of concern with highly flexible sanitary napkins, such as the extensible sanitary napkin described herein. The tension placed on the main body portion 22 by the wrapping of the flaps 24 can cause the end regions 32 and 34 of the main body portion 22 to become unattached from the adhesive attachment to the wearer's undergarment. This results in the end edges 28 of the main body portion 22 folding or rolling over on top of other portions of the main body portion 22.

Figure 6:
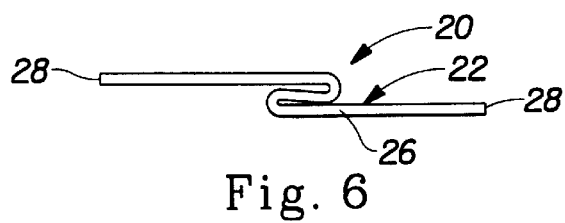
FIG. 6 is a schematic side view of a flexible and extensible sanitary napkin that shows some of the problems the sanitary napkin can be subject to if it is not provided with the improved features of the present invention.

Still another problem seen in highly flexible sanitary napkins that is caused by the tension created by folding the flaps 24 is shown in FIG. 6. FIG. 6 shows a highly flexible sanitary napkin 20. While it is understood that the sanitary napkin 20 has flaps, it is shown in FIG. 6 without flaps for simplicity since the effect of the forces on the main body portion 22 is primarily of interest. As shown in FIG. 6, the tension created by folding the flaps 24 can pull one or both of the ends of the main body portion 22 inward toward the transverse centerline and cause portions of the main body portion 22 to fold over one another. The panty fastening adhesive on the garment-facing side 20B of the sanitary napkin can cause the folded over portions to adhere to the underlying portions of the main body portion 22. This may be referred to herein as "Z-folding" in view of the shape taken by the main body portion.

The direction of the primary vector component of extensibility in the corner regions 86 substantially reduces or eliminates these problems. It has been determined that most of these problems can be attributed to the tension forces that are exerted between the end regions of the main body portion 22 and the portions of the flaps 24 secured by the flap adhesives 82. The direction of the primary vector component of extensibility in the corner regions 86 is preferably in a direction that is generally parallel to the line of tension between these portions of the sanitary napkin. This extensibility reduces the tension between the end regions of the main body portion 22 and the portions of the flaps 24 secured by the flap adhesives 82. In addition, the direction of extensibility of the corner regions 86, like that of the second and third regions of extensibility, is also inwardly-oriented toward the flap transverse centerline $T_1$. Some prior efforts were directed toward orienting the extensible portions of the flaps in the same direction as the extensibility of the wearer's panty elastics. The extensibility provided to the sanitary napkin described herein is in a direction which crosses that of the wearer's panty elastics, and is more nearly perpendicular to the same.

It should also be noted that in the preferred embodiment shown in the drawings, the corner regions 86 and the second and third regions of extensibility 46 and 48 are preferably elastically extensible due to the formation of the strainable network regions therein. This is accomplished without attaching conventional elastic strands to the material comprising these portions of the sanitary napkin. Further, the less extensible bands (first network regions) do not place tension on these regions of the sanitary napkin in such a manner to cause the flaps to fold underneath the absorbent core.

The corner regions 86 of the flaps of the sanitary napkin 20 shown in the drawings together with the adjacent second and third regions of extensibility 46 and 48, are preferably capable of extensibility in a direction parallel to the first network regions 64 therein, in the following amounts at the forces specified: 5% elongation under a force of less than or equal to about 75 grams; 10% elongation under a force of less than or equal to about 150 grams; 15% elongation under a force of less than or equal to about 175 grams; and 25% elongation under a force of less than or equal to about 250 grams. The corner regions 86 of the flaps 24 and the adjacent second and third regions of extensibility 46 and 48, in the embodiment shown, are preferably elastically extensible. The corner regions 86 of the flaps 24 and the adjacent second and third regions of extensibility 46 and 48 shown in the drawings may have a small amount of set (up to about 10%) after they have been extended.

Numerous alternative embodiments of the flaps 24 shown in the drawings are possible. In (less preferred)

embodiments, the corner regions of the flaps 24, rather than having the inwardly-oriented extensibility described herein, could have regions that are extensible entirely in the transverse direction, entirely in the longitudinal direction, or outwardly in a direction between the longitudinal and transverse directions. In addition, it is also possible in less preferred embodiments, to eliminate the less extensible bands comprising the first regions 64 of the strainable network from the corner regions 86 of the flaps. The less extensible bands can also be eliminated from the other portions of the sanitary napkin, including the main body portion 22. It is also within the scope of the present invention for the flaps described herein to be utilized on conventional non-extensible absorbent articles.

The garment surface 20B of the sanitary napkin 20 may include, and preferably does include, fasteners for attaching the sanitary napkin to the wearer's undergarment. FIG. 1 shows the central pad fastener 80 which is adapted to secure the main body portion 22 of the sanitary napkin to the crotch region of an undergarment. Any types of fasteners known in the art, such as adhesive fasteners and mechanical fasteners can be used as the central pad fastener 80. Fasteners comprising adhesives have been found to work well for this purpose, with pressure-sensitive adhesives being preferred.

Figure 4:
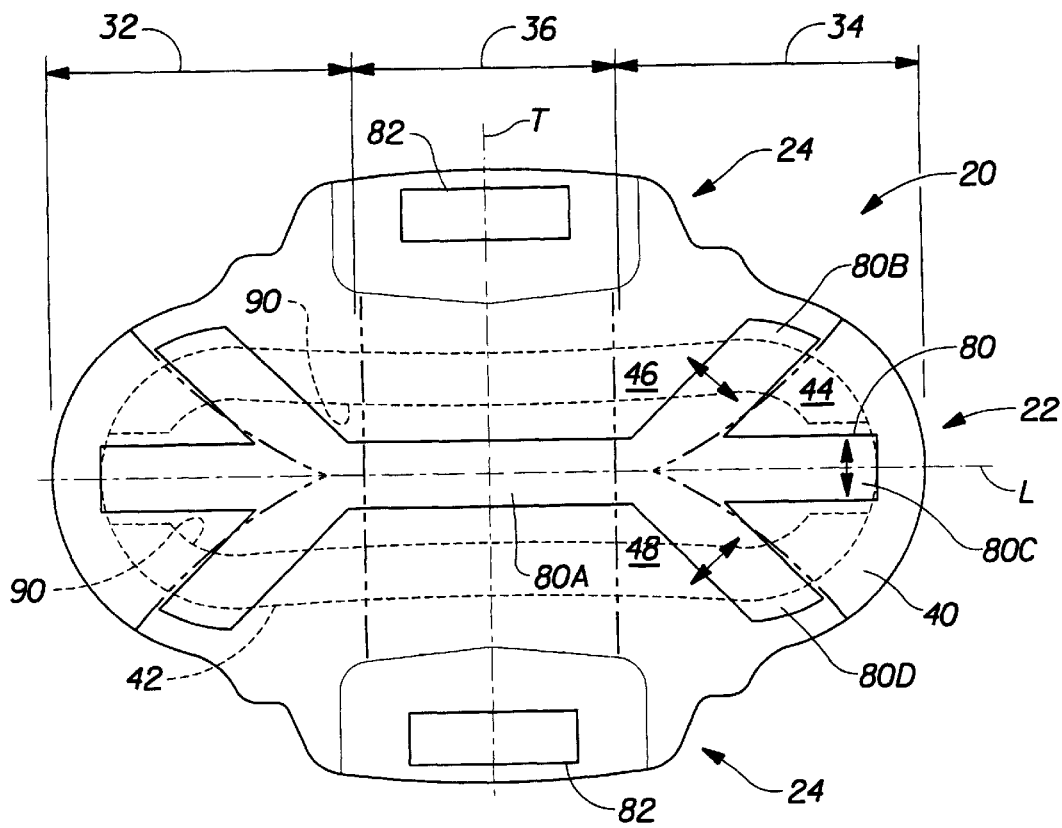
FIG. 4 is a bottom plan view of the sanitary napkin shown in FIG. 1 shown with the strainable network regions omitted from the backsheet for simplicity of illustration.

The central pad fastener 80 can be in any suitable configuration. Preferably, as shown in FIG. 4, the central pad fastener 80 has a configuration that comprises a longitudinally oriented zone of adhesive 80A having several "branches" 80B, 80C, and 80D extending therefrom. The branches 80B, 80C, and 80D lie in the end regions 32 and 34 of the main body portion 22 and preferably extend from the longitudinal centerline, L, toward the periphery 30 of the main body portion 22. In each end region, one of the branches of adhesive 80B, 80C, and 80D extends into each of the three regions of extensibility, 44, 46, and 48. Preferably, the branches of adhesive 80B, 80C, and 80D are oriented in a direction that is generally perpendicular to the primary direction of extensibility of the respective regions. This has been found to allow extensibility in the desired directions while firmly anchoring the sanitary napkin 20 in place in the wearer's undergarments. The adhesive can be applied to the backsheet 40 in any suitable manner. Preferably, in the embodiment shown, the adhesive comprising the various zones and branches of adhesive is an extensible hot melt adhesive, such as Fuller adhesive 2238 obtained from The H.B. Fuller Company, which is applied in a spiral pattern to provide a degree of extensibility.

The outer surface of the flaps 24, adjacent the distal edges 24B of the flaps, is preferably provided with a flap fastener, such as flap adhesive 82. The flap adhesive 82 is used to assist in maintaining the flaps 24 in position after they are wrapped around the edge of the crotch portion of the panty. While the flap adhesive 82 can be of any suitable size, it is preferably between about 60% and about 80% of the length of the distal portion 24B of the flaps 24. Suitable adhesive fasteners are described in greater detail in U.S. Pat. No. 4,917,697. The flaps 24 can be maintained in position by attaching the flaps 24 to the undergarment, or to the opposing flap.

The fasteners, central pad fastener 80 and flap fasteners 82, used with the present invention are not limited to adhesive attachment means. Any type of fastener used in the art can be used for such purpose. For example, the sanitary napkin 20 could be secured to the wearer's undergarment by mechanical fasteners, such as VELCRO hook material, or the fasteners described in U.S. Pat. No. 4,946,527 entitled "Pressure-Sensitive Adhesive Fastener and Method of Making the Same" issued to Battrell on Aug. 7, 1990, or U.S. Pat. No. 5,392,498 entitled "Non-Abrasive Skin Friendly Mechanical Fastening System" issued to Goulait, et al. on Feb. 28, 1995. For simplicity, however, the fasteners will be described in terms of adhesive attachment means.

The adhesive attachment means are respectively covered by removable release liners, central pad release liner and flap release liner, both designated 84. The pressure-sensitive adhesives should be covered with release liners 84 to keep the adhesives from sticking to extraneous surfaces prior to use. Suitable release liners are described in U.S. Pat. No. 4,917,697. In a preferred embodiment, the flaps 24 are folded over the topsheet and the flap adhesives 82 are covered by a single release paper. The adhesive attachment means on such flaps could, instead of being covered with a release liner, be releasably adhered to a release surface provided on some other portion of the sanitary napkin, including the main body portion, or the flaps, or a separate component attached to the main body portion or the flaps. For example, the flaps 24 could be folded and tucked as described in U.S. Pat. No. 5,281,209 issued to Osborn, et al. on Jan. 25, 1994. The sanitary napkin 20 may additionally be provided with a particularly preferred release liner which also serves as an individual package for wrapping the sanitary napkin as is described in U.S. Pat. No. 4,556,146 issued to Swanson, et al.

The sanitary napkin 20 is utilized by removing the release liners 84 and placing the sanitary napkin 20 in a panty. The main body portion 22 is placed in the crotch portion of the panty with one end of the main body portion 22 extending towards the front section of the panty and the other end towards the back section of the panty. The backsheet 40 is placed in contact with the inner surface of the center of the crotch portion of the panty. The central pad adhesive fastener 80 maintains main body portion 22 in position. The flaps 24 are then folded around the side edges of the panty. The flap adhesives 82 secure the flaps 24 to the underside of the panty or to the opposing flap.

Figure 7:
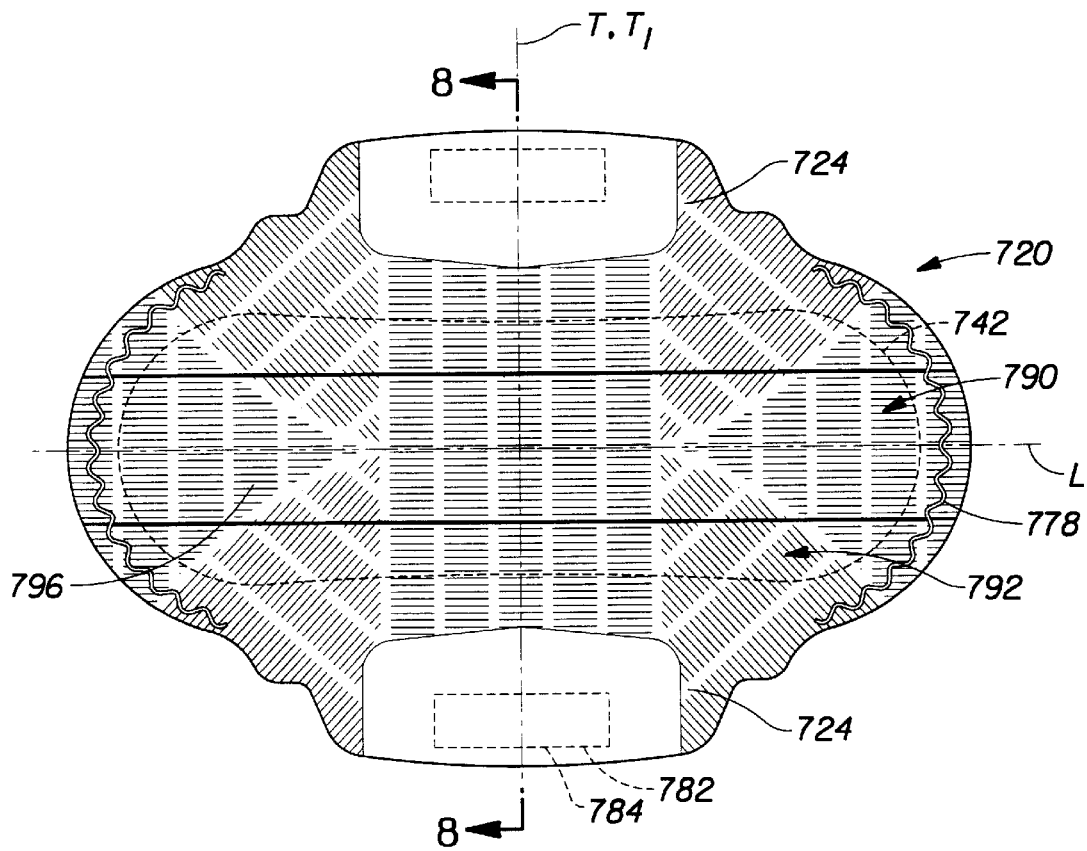
FIG. 7 is a top plan view of a preferred compound sanitary napkin according to the present invention.
Figure 8:
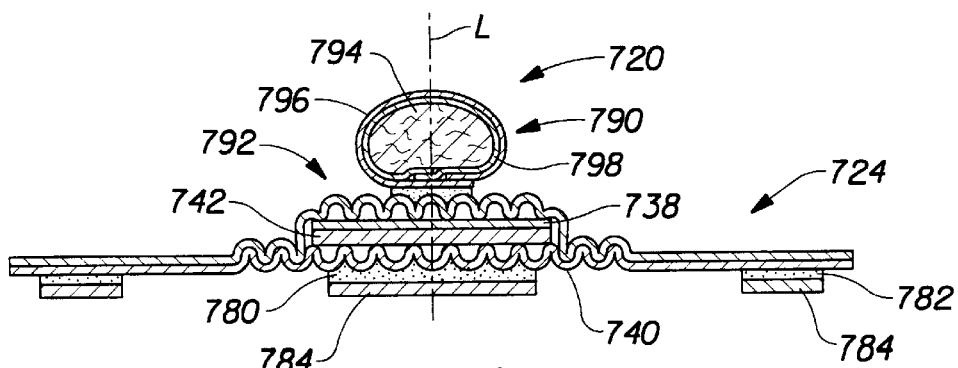
FIG. 8 is a cross-sectional view of the compound sanitary napkin shown in FIG. 7 taken along line 8—8, and shown without corrugations in topsheet and backsheet for simplicity.

Other embodiments of the absorbent articles described herein are also possible. For example, FIGS. 7 and 8 show an embodiment of an absorbent article in the form of a compound sanitary napkin 720. The compound sanitary napkin 720 comprises a primary absorbent component (or "core tube") 790 which is joined to the body-facing side of a secondary absorbent component (or "base pad") 792. The primary absorbent component 790 is preferably intended to absorb the bulk of bodily fluids discharged by the user. The base pad 792 primarily functions to protect the user's garments from soiling by absorbed fluids which may be expelled from the primary absorbent component 790 or which inadvertently bypass the primary absorbent component 790.

In the embodiment shown in FIGS. 7 and 8, the primary absorbent component 790 comprises an absorbent structure, such as absorbent core 794, and an outer cover 796 that wraps the absorbent core 794. The outer cover 796 can comprise any of the materials described above as being suitable for the topsheet of the embodiment shown in FIGS. 1–4.

The absorbent core 794 can comprise any material suitable for absorbing or retaining liquids (e.g., menses and/or urine). Examples of suitable absorbent material include comminuted wood pulp which is generally referred to as airfelt; creped cellulose wadding; meltblown polymers including coform; chemically stiffened, modified or crosslinked cellulosic fibers; synthetic fibers such as crimped polyester fibers; peat moss; tissue including tissue wraps and tissue laminates; absorbent foams; absorbent sponges, superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures).

The primary absorbent component 790 may further comprise an optional acquisition layer 798 shown in FIG. 9. The acquisition layer 798 may be a separate component positioned between the outer cover 796 and the absorbent core 794, or it may be an integral part of a composite outer cover. The acquisition layer 798 may serve several functions including improving the wicking of exudates over and into the absorbent core 794 and/or containing absorbent material in the absorbent core 794.

The base pad 792 of the compound sanitary napkin 720 shown in FIGS. 7 and 8 preferably comprises the sanitary napkin 20 shown in FIGS. 1–4. The elements of the base pad 792 shown in FIGS. 7 and 8 that have been discussed above in conjunction with FIGS. 1–4 are designated with the number 700 preceding the same reference numbers used in FIGS. 1–4. The primary absorbent component 790 may, but need not be extensible. As shown in FIG. 7, in one preferred embodiment, the outer cover 796 of the primary absorbent component 790 comprises the same material used for the topsheet 738 of the base pad. Preferably, after the outer cover 796 is wrapped around the primary absorbent component 790, the regions of extensibility in the outer cover 796 are aligned directly over those of the topsheet 738 on the base pad 792 as shown in FIG. 7.

Compound sanitary napkins (without the extensibility described herein) are further described in U.S. Pat. No. 4,425,130 issued to DesMarais on Jan. 10, 1984, and in Statutory Invention Registration H1614 entitled "Body Fitting Compound Sanitary Napkin," published in the name of Mayer, et al. on Nov. 5, 1996.

In alternative embodiments, the components, such as the topsheet and backsheet of the absorbent articles described herein can optionally be replaced with any suitable (extensible) components described in the patents and patent applications incorporated by reference herein. For instance, in one non-limiting example, the backsheet with the strainable network regions described herein could be replaced with a liquid impervious extensible adhesive film, if desired. In addition, the absorbent articles described herein can optionally be provided with any of the characteristics and/or features described in the patents and patent applications incorporated by reference herein.

For example, other embodiments of the sanitary napkin 20 may be extensible in the various directions specified herein in the amounts described in U.S. Pat. No. 5,611,790 under the forces associated with wearing the sanitary napkin in a pair of panties. The sanitary napkin of the present invention can also be provided with any of the other features of the sanitary napkins described in U.S. Pat. No. 5,611,790 including, a structure that provides a "force wall" to prevent elongation past a certain amount without substantial increases in the amount of force applied to the sanitary napkin.

In these or other embodiments, the absorbent articles described herein can be provided with zones of extensibility in any other suitable configurations, or that stretch in any other suitable directions. The absorbent articles described herein can also be provided with various regions that stretch more or less than other regions for improved contact with the wearer's body, or for other purposes. Some examples of absorbent articles having such regions are described in the patents and patent applications incorporated by reference herein. For instance, sanitary napkins having regions of differential extensibility are described in U.S. Pat. No. 5,611,790 issued to Osborn, et al. Sanitary napkins having improved mechanisms for maintaining the sanitary napkin in contact with the wearer's body are described in U.S. patent application Ser. No. 08/383,536, filed in the name of Osborn, et al. on Feb. 2, 1995 (P&G Case 5151R) PCT Publication No. WO 95/20931, published Aug. 10, 1995.

The absorbent articles described herein can also be provided with regions that are stiffer or more flexible than other regions for improved body contact or other purposes. For example, FIG. 4 shows that the sanitary napkin 20 can be provided with optional stiffeners 90. The optional stiffeners 90 are preferably provided along at least a portion of the perimeter of the absorbent core 42, particularly along the longitudinal side edges 42A of the absorbent core 42. The optional stiffeners can be positioned inside the entire periphery of the absorbent core 42. Preferably, however, as shown in FIG. 4, the optional stiffeners 90 are not present along the longitudinal centerline L of the sanitary napkin 20.

In the embodiment shown in FIG. 4, the optional stiffeners 90 comprise a 60% polyester/40% rayon material available from fabric stores known as PELLON® Craft-Bond material sold by Freudenbert Nonwovens. The PELLON stiffening material preferably has a caliper of 0.35 mm, a flexure resistance of about 33 grams, and a Taber stiffness of about 0.85 g/cm. The PELLON stiffening material can be positioned between any of the layers of the sanitary napkin 20. The PELLON stiffening material is preferably positioned underneath the absorbent core 42 and joined to the underside of the absorbent core by adhesives, such as Fuller adhesive 2031.

The optional stiffeners 90 shown in FIG. 4 provide the longitudinal side edges of the absorbent core and the end regions 32 and 34 of the sanitary napkin 20 with an additional degree of stiffness to reduce undesirable bunching and reduce or eliminate the problem of end edge "roll over" discussed above. The optional stiffeners 90 will also provide the zone of the sanitary napkin which lies along the longitudinal centerline of the same with increased "lift" for improved contact with the wearer's body. Without wishing to be bound by any particular theory, it is believed that the increased lift can be attributed to the fact that due to the presence of the stiffeners 90, all of the lift is concentrated in the region along the longitudinal centerline between the inside edges of the stiffeners 90. The stiffer areas on the outer perimeter or sides of the sanitary napkin can also help to secure sanitary napkin to the wearer's panty.

It is recognized, however, that if an inextensible material such as PELLON is used for the stiffness, the extensibility of the stiffened regions of the sanitary napkin 20 will be reduced or eliminated. This embodiment of the sanitary napkin 20 can, however, still function effectively particularly when a gap is left between the stiffeners 90 along the longitudinal centerline L. Such an embodiment is still capable of extension along the longitudinal centerline, and in the diagonal direction as specified above. This embodiment also allows the first region of extensibility 44 in the end regions 32 and 34 to extend transversely. If it is not desirable to affect the extensibility of the sanitary napkin, a stiffening material can be chosen which has a degree of extensibility.

In addition, in alternative embodiments, instead of being provided with flaps, the absorbent article could be provided with undergarment covering components or ("side wrapping elements") that preferably have a smaller span than conventionally sized flaps and that do not have to be manipulated by the wearer when placed in the wearer's undergarments. Absorbent articles having side wrapping elements are described in U.S. Pat. No. 5,584,829 entitled "Absorbent Articles Having Panty Covering Components That Naturally Wrap the Sides of Panties" issued to Lavash, et al. on Dec. 17, 1996; U.S. patent application Ser. No. 08/124,180 entitled "Absorbent Articles Having Panty Covering Components Comprising Extensible Web Materials Which Exhibit Elastic-Like Behavior" filed Sep. 17, 1993, in the name of Mansfield, et al. (PCT Publication No. WO 95/07675, published Mar. 23, 1995); and U.S. Pat. No. 5,558,663 entitled "Absorbent Articles Having Undergarment Covering Components With Zones of Extensibility" issued to Weinberger, et al. on Sep. 24, 1996.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

It should also be understood that all of the limits and ranges specified herein include all narrower ranges, limits, and amounts that are within the specified limits and ranges and that such narrower ranges and limits may be claimed even though those limits and ranges are not separately listed.

TEST METHODS

Unless otherwise indicated, all the following tests are performed on samples that have been conditioned by leaving them in a room at 50% relative humidity and at 73° F. (23° C.) for a period of two hours prior to the test. The tests should be performed under similar conditions.

Absorbent Material Capacity

Absorbent capacity of the absorbent material may be determined as follows.

A rectangular sample measuring 2½ inches by 3 inches (6.4 cm by 7.6 cm) of absorbent material is obtained. The sample is weighed to the nearest 0.1 gram. The sample is then totally submerged in distilled water by dunking it in a distilled water-filled tray, such that the sample is not bent or otherwise twisted or folded. The sample is submerged for 20 minutes. The sample is removed from the distilled water and suspended for two minutes to allow the distilled water to drain out of the sample. The sample is then weighed to the nearest 0.1 gram and the dry weight of the sample is subtracted. The difference in grams is the absorbent capacity of the sample. The absorbent capacity can then be expressed as a ratio of the absorbent capacity to the dry weight of the sample in grams/gram.

Extensibility Tests

The following extensibility tests of the absorbent material or sanitary napkin (or other absorbent article) utilize a constant rate of elongation tensile testing apparatus such as an Instron model #1122 tensile testing instrument, or an EME Tensile Tester, Model No. 559A obtained from EME, Inc., P.O. Box 187, Newbury, Ohio 44065.

The testing instrument is preferably provided with a computer that provides an LCD readout of the distance the ends of the clamps are spaced from a reference home position and the forces on the sample when the clamp are spaced various distances from the home position.

The samples are carefully handled to avoid any stretching of the same prior to performing the tests. If the tests are performed on absorbent articles, the tests should each be repeated with samples taken from five separate products of the same type. If any of the samples fall within the claimed range or limit, the product will be considered to fall within the scope of the appended claims.

A. Absorbent Material Extensibility—One Inch (2.5 cm) Strip Tests

Samples for Measuring Extensibility

The samples are preferably taken from a web of absorbent material before it is incorporated into the absorbent article. If this is not possible, the absorbent material samples may be obtained by carefully removing the absorbent material from the absorbent article. This can be done by peeling away other portions of the absorbent article while being careful not to damage the absorbent material or do anything else that will affect the extensibility of the same.

The samples are obtained by cutting a 1.0 inch (2.54 cm.) wide strip from the absorbent material using a JDC Precision Sample Cutter, Model #1-12 available from Thwing-Albert, Philadelphia, Pa. The term "absorbent material", as used herein, refers to material that is generally used as the primary absorbent component of the product, such as the absorbent core of the product. It also includes absorbent materials that serve a wicking or storage function.

The strip used as the sample for measuring longitudinal extensibility should be taken from a portion of the absorbent article that is centered about the longitudinal centerline of the absorbent article. The length of the strip should run the full length of the portion of the absorbent article from which the sample is taken.

If the sample can be taken from a web of absorbent material before the absorbent material is placed into the absorbent article, a 1"×4" strip of fabric should be cut so that its extensibility runs in the same direction that it will be oriented in the assembled absorbent article. A sample for measuring longitudinal extensibility should be cut from a first sample of the absorbent material. The sample for measuring transverse extensibility should be cut from a second sample of the absorbent material of the same type as the first (i.e., an identical material or product). Likewise, the sample for measuring diagonal extensibility should be cut from a third sample of the absorbent material or absorbent article of the same type as the first (i.e., an identical material or product).

The strip used as the sample for measuring transverse extensibility is a 1.0 inch wide strip that is cut from the absorbent material that runs (or will be positioned in the assembled absorbent article so that it runs) parallel to the transverse centerline of the absorbent article. The strip used as the sample for measuring the transverse extensibility can be cut through any one inch wide section of the absorbent material that runs parallel to the transverse centerline. The sample need not run along the transverse centerline.

The strip used as the sample for measuring the diagonal extensibility is cut through a one inch wide section of the absorbent material that runs (or will be positioned so that it runs) at a 45 degree angle to the longitudinal centerline of the absorbent article.

Procedure

Lay the sample unrestrained on a table. Measure the length of the sample (the dimension of the sample that runs perpendicular to the one inch width dimension) to the nearest 0.1 inch (0.25 cm).

Clamp each end of the sample in the tensile testing apparatus using 1 inch (2.54 cm.) wide clamps. The clamps of the tensile tester are set so that they will be pulled away from each other in opposite directions (that is, they will pull at an angle of 180 degrees). The sample should be centered in the clamps and the clamping pressure should be sufficient to prevent any slippage of the sample in the clamps (this applies to all of the extensibility test methods). The sample should be clamped so that the outermost edge (i.e., the free end) of the clamps are approximately 0.5 inches (about 1.3 cm) inward from the end edges of the absorbent material.

Set the gauge length of the tensile tester to the length of the absorbent material (as measured above) less the amount of absorbent material clamped into each of the clamps (typically 1 inch). A gauge length of 2 inches (5 cm) has been found to be suitable. Initiate the elongation with a cross head speed of 20 inches/minute (51 cm/minute). When the sample reaches the gauge length, tare the load cell of the testing apparatus to zero. Set the trigger point to begin collecting data at 5 grams force.

The force and extensibility measurements are taken at the desired times, and the test is completed. The force, for the purpose of the appended claims is the actual force reading on the testing apparatus when the above procedure is followed. The results are expressed in grams/inch or grams/cm.

If the one inch strips of absorbent material are extensible in the amounts and under the forces specified in the claims in the following three directions: the longitudinal direction, along any cross-section in the transverse direction, and in the 45 degree diagonal direction, the absorbent material will be considered to be omni-directionally extensible.

B. Method to Measure Extensibility of Absorbent Article or Various Portions Thereof This test is used to measure the extensibility of the absorbent article, or various regions of the same. The type of test used for this purpose is known as a "grab test". It involves clamping portions of the absorbent article in the clamps of the tensile tester and exerting a tensile force on either the entire absorbent article, or the desired regions of the same.

The sample used for this test is the entire absorbent article. Separate samples of the absorbent article of the same type (i.e., identical products) should be used for measuring the different directions of extensibility of the absorbent article, or the extensibility of the different regions of the same.

The absorbent article can be tested for: the longitudinal extensibility of the absorbent article; the transverse direction extensibility of the absorbent article (both along the transverse centerline, and in the end regions of the absorbent article); the diagonal extensibility of the absorbent article; the extensibility in the corner regions of the flaps and those regions of extensibility of the main body portion adjacent to the flaps; and the extensibility of the crimp seal.

In this test, one inch (2.54 cm) wide clamps are used in the testing machine. If the absorbent article has regions with different directions of extensibility, and it is desired to measure the extensibility of the various regions, then care should be taken to place both of the clamps entirely within the desired region. If this is not possible, the clamps should be placed as nearly as possible entirely within the desired region.

In testing for the longitudinal extensibility of the absorbent article, the clamps should be centered about the longitudinal centerline of the absorbent article. In testing for the transverse extensibility of the central region of the absorbent article, the clamps should be centered about the transverse centerline. In testing for the transverse extensibility of the end regions of the absorbent article, the clamps should be placed in the end regions so that the elongation will be parallel to the transverse centerline. In testing for diagonal extensibility of the absorbent article, the clamps are placed in opposite corners of the main body portion of the absorbent article so that the primary vector component of the elongation forces will pass through the intersection of the longitudinal and transverse centerlines of the absorbent article.

In testing for the extensibility between the corner regions of the flaps and adjacent regions of extensibility of the main body portion of the absorbent article, the clamps should be aligned with the applicable angle, A. One clamp is placed in the flap and the other clamp is placed in the region of extensibility of the main body portion. In testing for the extensibility of the crimp seal, the clamps are placed centered about the crimp seal so that the elongation will be applied in the direction of extensibility of the region containing the crimp seal.

The absorbent article should be clamped so that the outermost edge (i.e., the free end) of the clamps are approximately 0.5 inches (about 1.3 cm) inward from the end edges of the absorbent material in the various regions. If, however, there is no absorbent material in a portion of the region (such as the one clamp that lies in the corner region of the flaps, or if both clamps lie in the region of the crimp seal), clamping inside the edges of the absorbent material is not required.

Set the gauge length of the tensile tester to the length of the absorbent material less the amount of absorbent material clamped into each of the clamps. Initiate the elongation with a cross head speed of 20 inches/minute (51 cm/minute). When the sample reaches the gauge length, tare the load cell of the testing apparatus to zero.

The force and extensibility measurements are taken at the desired times, and the test is completed. The results are expressed in grams.

While particular embodiments of the present invention have been illustrated and described, it would be obvious to those skilled in the art that various other changes and modifications can be made without departing from the spirit and scope of the invention.

What is claimed is:

1. An absorbent article for wearing in an undergarment, said absorbent article having a pair of longitudinal side edges and a pair of end edges forming the periphery of said absorbent article, said absorbent article comprising:

a liquid pervious topsheet having at least one extensible region therein;

a liquid pervious backsheet having at least one extensible region therein, said backsheet being at least partially peripherally joined to said topsheet; and an absorbent core positioned between said topsheet and said backsheet, said absorbent article further comprising a crimp seal that is used to at least partially peripherally join said at least one extensible regions of said topsheet and backsheet, wherein said crimp seal has a sinusoidal plan view configuration and permits said extensible regions of said topsheet and backsheet to extend when tensile forces act on the same.

2. The absorbent article of claim 1 wherein said crimp seal is capable of extending greater than about 10% in at least one direction under forces greater than or equal to about 50 grams and less than or equal to about 500 grams.

3. The absorbent article of claim 2 wherein said crimp seal is capable of such extension under forces of less than or equal to about 200 grams.

4. An extensible absorbent article for wearing in an undergarment, said absorbent article having a pair of longitudinal side edges and a pair of end edges forming the periphery of said absorbent article, said absorbent article comprising:

an extensible liquid pervious topsheet;

an extensible liquid pervious backsheet at least partially peripherally joined to said topsheet; and an absorbent core positioned between said topsheet and said backsheet, said absorbent article further comprising an extensible crimp seal that is used to at least partially peripherally join said topsheet and backsheet, said extensible crimp seal having a sinusoidal configuration.

* * * * *